United States Patent

Dragan et al.

[11] Patent Number: 5,876,384
[45] Date of Patent: Mar. 2, 1999

[54] MICRO ASPIRATOR

[76] Inventors: William B. Dragan, 85 Burr St., Easton, Conn. 06612; John J. Discko, Jr., 50 Laura Rd., Hamden, Conn. 06514

[21] Appl. No.: 958,729

[22] Filed: Oct. 27, 1997

Related U.S. Application Data

[63] Continuation of Ser. No. 539,544, Oct. 5, 1995, abandoned.

[51] Int. Cl.$^6$ .................................................. A61C 17/06
[52] U.S. Cl. ............................. 604/264; 433/91; 433/96; 604/93
[58] Field of Search ............................. 604/289; 606/106, 606/107; 433/91, 96

[56] References Cited

U.S. PATENT DOCUMENTS

| | | | |
|---|---|---|---|
| D. 359,119 | 6/1995 | Dragan et al. . | |
| 4,002,174 | 1/1977 | Reed et al. | 604/239 |
| 4,204,328 | 5/1980 | Kutner | 433/96 |
| 4,586,900 | 5/1986 | Hymanson et al. | 433/96 |
| 4,878,900 | 11/1989 | Sundt | 433/91 |
| 4,990,140 | 2/1991 | Black | 604/239 |
| 5,123,840 | 6/1992 | Nates et al. | 433/91 |
| 5,295,830 | 3/1994 | Shen et al. | 433/91 |
| 5,324,273 | 6/1994 | Discko, Jr. | 604/240 |
| 5,336,088 | 8/1994 | Discko, Jr. . | |
| 5,439,449 | 8/1995 | Mapes et al. | 604/264 |
| 5,470,318 | 11/1995 | Griffith, III et al. | 604/93 |
| 5,599,333 | 2/1997 | Atkinson | 604/326 |

Primary Examiner—Wynn Wood Coggins
Assistant Examiner—L. Thanh
Attorney, Agent, or Firm—Fattibene & Fattibene; Arthur T. Fattibene; Paul A. Fattibene

[57] ABSTRACT

This invention is directed to a micro aspirator for use in performing microsurgery for the removal of blood, debris and fluids from around the micro surgical site. The micro aspirator includes an elongated flexible tube which is preferably transparent, which is adapted to be connected to a negative pressure source and an aspirating tip formed as a plastic hub having a connected needle or cannula with a gauge ranging between 10 to 30 connected to the end of the flexible tube. The plastic hub may be either detachably or fixedly secured to the end of the flexible tube, with the needle or cannula being formed of a readily bendable material that can be easily bent by the operator or surgeon to any desired angle.

1 Claim, 1 Drawing Sheet

MICRO ASPIRATOR

This application is a continuation, of application Ser. No. 08/539,544, filed Oct. 5, 1995, now abandoned.

FIELD OF THE INVENTION

This invention relates to a micro aspirator, and more particularly to a micro aspirator for use in a micro surgical procedure to remove blood, fluid and debris from a micro surgical site.

PROBLEM AND PRIOR ART

In a surgical procedure, the removal of blood, fluid and debris is essential for maintaining visibility about the surgical sight during an operation. Generally, this is effected by use of a high speed suction or vacuum device. Usually, the end of the suction tube was provided with a removable aspirating nozzle that was either disposable or autoclavable. Generally, such known aspirator nozzles were quite large, and are primarily used where the field of surgery is large and the excessive blood, fluid and debris readily accessible. In the field of micro surgery such as an apicoectomy, which a dental surgeon performs on the root end of a tooth, e.g., to eliminate an abscess, a significant problem is encountered in attempting to evacuate blood and fluid accumulating in such a restricted area. Another problem encountered in a micro surgical root canal endodontic procedure is the drying of the canal. Heretofore, the normal procedure was to use paper points for drying the canal. Such paper points were inserted into the canal to blot up any excess moisture or liquids. These points are relatively expensive and numerous such paper points are required to satisfactorily dry the canal before the root canal can be filled and sealed. Access to such micro surgical sites is extremely limited, and the standard aspirator nozzles are not adequate or suitable to properly aspirate the restricted surgical site.

Because of the restricted surgical site, it is desirable to have an aspirator that can be variably configured so as to reach the difficult, hard to reach micro surgical sites. The known aspirator nozzles do not have the ability to be readily configured by the surgeon to meet a desired need.

Also, the known aspirators were generally made of metal and opaque. As a result, the surgeon did not have the ability to see any blockage that might occur, as by clotting of the blood or debris, prior to the aspirator malfunctioning due to clotting and/or blockage.

SUMMARY OF THE INVENTION

An object of this invention is to provide a micro aspirator that is readily disposable and replaceable for use in micro surgical procedures, e.g., an apicoectomy, endodontics, and the like.

Another object is to provide a micro surgical aspirator having a micro tip with a small needle cannula which can be readily bent without occluding the lumen.

Another object is to provide a micro surgical aspirator having a micro tip having variable size cannula lumens that can be readily interchangeably connected to the aspirating tube or conduit.

Another object is to provide a micro aspirating tip that is readily interchangeable and disposable to prevent cross contamination.

Another object is to provide a micro aspirator which includes a flexible transparent conduit or tube to provide clear visibility to determine whether any blockage has occurred and which can be readily flushed with water.

Another object is to provide a micro aspirator comprised of a disposable aspirating tube and a fixedly connected micro tip with a needle cannula whereby the entire aspirator of tube and tip is rendered readily disposable after each use.

Another object of this invention is to eliminate or minimize the need for the use of relatively expensive paper points to remove moisture or liquid from a root canal in an endodontic procedure.

The foregoing objects and other features and advantages are attained by providing a micro aspirator having a transparent aspirating conduit or tube which is suitably connected to a source of negative pressure or vacuum. Preferably, the aspirating tube or conduit is formed of a readily flexible plastic tube of generally uniform wall thickness of any predetermined length which is simply terminated at one end as by cutting. Connected to the free end of the aspirating tube or conduit is a micro aspirating tip that includes a hub having a bore extending therethrough. The proximal end of the hub is provided with an externally tapered end portion which is arranged to be either detachably connected, e.g. by friction, or fixedly secured to the terminal or free end of the flexible aspirating tube or conduit. Connected to the distal end of the hub is a small gauge cannula or needle having a gauge ranging between 10 to 30. The needle or cannula is annealed so that it can be easily bent to any desired angle by the surgeon or user without occluding the aspirating passage or lumen of the cannula. The arrangement is such that the hub of the aspirating tip in one form of the invention is frictionally secured to the aspirating tube by insertion of the externally tapered end into the end of the aspirating conduit or tube, so as to render it readily detachable and disposable. In another form of the invention, the micro tip is fixedly secured whereby the tube and connected tip is rendered readily disposable. The needle or cannula, which is readily bendable, is sufficiently small so as to reach a micro surgical site, e.g., the root end of a tooth or root canal.

IN THE DRAWINGS

DETAILED DESCRIPTION OF THE PREFERRED EMBODIMENTS

Figure 1:
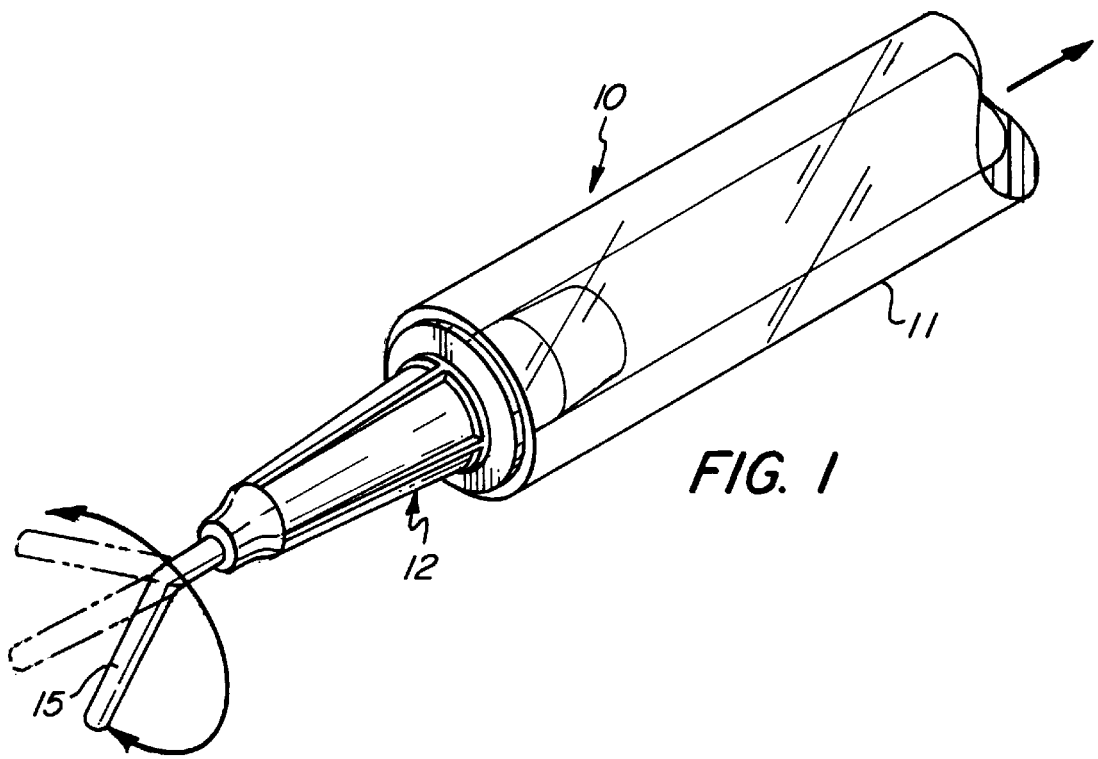
FIG. 1 is a perspective view of a micro aspirator embodying the present invention.
Figure 2:
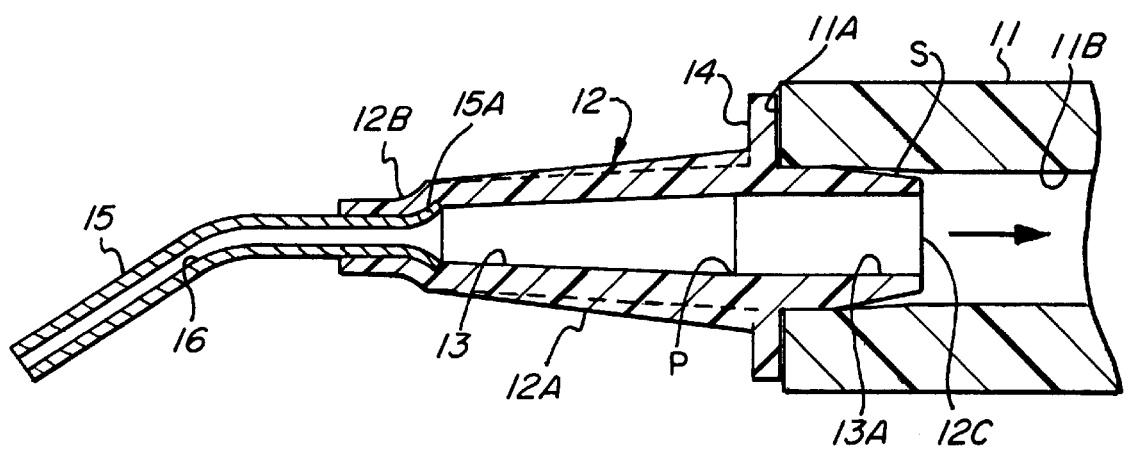
FIG. 2 is a longitudinal sectional view of the micro aspirator tip and connected tube.

Referring to the drawings, there is shown in FIGS. 1 and 2 a micro aspirator 10 which embodies the present invention. As shown, the micro aspirator 10 includes an elongated flexible plastic tube or conduit 11, which is suitably connected to a source of negative pressure or vacuum, not shown. Preferably, the aspirating tube or conduit is formed of a clear plastic material and readily transparent so that a surgeon may see the flow of blood, fluid or debris being evacuated from the surgical site. As shown in FIG. 2, the flexible tube or conduit is formed with a generally uniform wall thickness extending throughout the length thereof and having a terminal end 11A.

Connected to the terminal end 11A of the tube or conduit 11 is a readily expendable micro aspirating tip 12. The micro aspirating tip 12 includes a generally elongated hub 12A having a bore 13 extending therethrough and an attached cannula 15 to form an integral unit or assembly. As shown in FIG. 2, the bore 13, starting at a predetermined medial point, e.g., at a point "P", tapers inward toward the distal end 12B. Bore portion 13A, extending toward the proximal end 12C from point "P", is generally cylindrical. As shown in FIG. 2, the external surface "S" of the proximal end 12C tapers inwardly or converges slightly toward the proximal end 12C. Intermediate the ends of the elongated hub 12A, the tip 12 is provided with a laterally outwardly extending flange 14 which functions as a stop when the tip 12 is fitted to the free or terminal end 11A of the conduit or tube 11. In one embodiment of the invention, it will be understood that the external diameter of the proximal end 12C of the hub 12A is slightly greater than the internal diameter of the flexible conduit to provide a forced or friction fit therebetween. In this form of the invention, the tip 12 is rendered readily detachably connected to the terminal end 11A of the aspirating conduit or tube 11 by frictionally inserting the proximal end 12C of the hub into the bore 11B of the conduit 11. In another form of the invention, the micro tip 12 is fixedly secured to the aspirating conduit, e.g. by bonding, adhesive or the like.

Fitted to and extending through the distal end of the bore 13 of the hub 12A is a small gauge cannula or needle 15 preferably formed of a metallic material having a gauge size ranging between 10 to 30. The cannula or needle 15 is normally straight when inserted through the proximal end of the bore 13 in the assembly of the tip 12 whereby the cannula 15 is extended through the distal end 12B of the hub 12A. As shown, the proximal end 15A of the cannula 15 is flared outwardly whereby it is imbedded and frictionally retained in the distal end 12B of the hub 12A. As the cannula is annealed, it is readily bendable to any desired angle by the user or surgeon, as shown in FIG. 1 without occluding the passageway or lumen 16 extending therethrough. The cannula can also be readily rotated relative to the hub 12A of the micro tip, as it is frictionally retained in the distal end 12B of the hub 12A.

The aspirator tip 12 can be rendered readily detachable or fixedly secured to the end 11A of the aspirating tube 11. The construction of the aspirator tip 12 is such that if detachably connected, it can be rendered readily expendable after use. If fixedly secured to the aspirating tube 11, the tube and fixedly connected micro tip are rendered readily disposable. Thus, the micro aspirator 10 described permits the surgeon to aspirate difficult, small, hard to reach micro surgical sites, such as in endodontic, apicoectomy procedures and the like, where previously aspiration was not generally feasible or difficult to achieve.

While the present invention has been described with respect to various embodiments, various modifications may be made without departing form the spirit or scope of this invention.

What is claimed is:

1. A micro aspirator for use in micro surgical root canal endodontic procedures comprising:

an elongated flexible transparent tube having one end adapted to be connected to a source of negative pressure;

a readily disposable aspirator tip connected to the other end of said tube;

said aspirator tip including an elongated hub and an attached cannula forming an integral assembly, said hub having a distal end and a proximal end; and said hub having a bore extending therethrough;

a radially outwardly extending flange connected to and circumscribing said hub intermediate said distal and proximal ends of said hub to limit the insertion of said hub relative to said tube;

said bore including a first portion tapering inwardly toward said distal end of said hub, and a connected second portion defining a substantially cylindrical bore extending toward said proximal end of said hub;

said proximal end of said hub having an external surface tapering inwardly toward said proximal end to facilitate insertion of said proximal end of said hub into said other end of said tube whereby said radially extending flange limits the insertion of said proximal end into said other end of said tube;

a cannula having a lumen extending therethrough inserted through the proximal end of said hub to extend out through said distal end of said hub for effecting the attachment of said cannula to said hub, said cannula being flared at its proximal end for rotatably connecting said cannula within said distal end of said hub;

said cannula having a gauge ranging between 10 to 30;

and said cannula being formed of an annealed metallic material whereby the cannula can be readily bent to any desired angle without occluding the lumen extending therethrough.

* * * * *